US012741100B2

(12) United States Patent
Xiong et al.

(10) Patent No.: US 12,741,100 B2
(45) Date of Patent: Sep. 22, 2026

(54) BOOSTER MECHANISMS SUITABLE FOR LIQUID CONTAINERS

(71) Applicant: SUZHOU HEALTHY TREE MEDICAL TECHNOLOGY CO., LTD., Suzhou (CN)

(72) Inventors: Changyan Xiong, Suzhou (CN); Sixian He, Suzhou (CN); Linchuan Yi, Suzhou (CN); Ming Hao, Suzhou (CN); Xingwu Li, Suzhou (CN); Kai Wang, Suzhou (CN)

(73) Assignee: SUZHOU HEALTHY TREE MEDICAL TECHNOLOGY CO., LTD., Suzhou (CN)

( * ) Notice: Subject to any disclaimer, the term of this patent is extended or adjusted under 35 U.S.C. 154(b) by 441 days.

(21) Appl. No.: 18/501,022

(22) Filed: Nov. 2, 2023

(65) Prior Publication Data

US 2024/0066236 A1 Feb. 29, 2024

Related U.S. Application Data

(63) Continuation-in-part of application No. PCT/CN2023/092040, filed on May 4, 2023.

(30) Foreign Application Priority Data

May 11, 2022 (CN) ......................... 202221126753.3

(51) Int. Cl.
*A61M 5/315* (2006.01)
*A61M 5/31* (2006.01)

(52) U.S. Cl.
CPC . *A61M 5/31576* (2013.01); *A61M 2005/3115* (2013.01)

(58) Field of Classification Search
CPC .......... A61M 5/31515; A61M 5/31511; A61M 5/31513; A61M 5/31576; A61M 5/315;
(Continued)

(56) References Cited

U.S. PATENT DOCUMENTS 3,834,387 A 9/1974 Brown
3,905,521 A * 9/1975 Mead .................... B01L 3/0217
422/923

(Continued)

FOREIGN PATENT DOCUMENTS

CN 213374422 U 6/2021
CN 114712624 A 7/2022

(Continued)

OTHER PUBLICATIONS

International Search Report in PCT/CN2023/092040 mailed on Jul. 9, 2023, 6 pages.

(Continued)

*Primary Examiner* — Kevin C Sirmons
*Assistant Examiner* — Leah J Swanson
(74) *Attorney, Agent, or Firm* — PORUS IP LLC

(57) ABSTRACT

The booster mechanism may include a liquid storage assembly. A tail end of the liquid storage assembly may be provided with a strike space. The strike space may be provided with a movable assembly. The movable assembly may be capable of performing an axial movement along the strike space. The tail end of the movable assembly may be provided with a booster assembly and a deformation space. A front end of the booster assembly may be provided with a deformation trigger assembly. A deformation gap may be between the deformation space and the deformation trigger assembly.

17 Claims, 9 Drawing Sheets

(58) Field of Classification Search

CPC ............ A61M 5/31; A61M 2005/3115; A61M 2005/3143; A61M 5/31501; A61M 5/31508; A61M 5/3151; A61M 5/31516; A61M 2005/2086

See application file for complete search history.

(56) References Cited

U.S. PATENT DOCUMENTS

| | | | | |
|---|---|---|---|---|
| 5,411,488 A * | 5/1995 | Pagay | ............... | A61M 5/31513 604/218 |
| 2015/0238700 A1* | 8/2015 | Jugl | .................. | A61M 5/31515 604/224 |
| 2017/0182253 A1* | 6/2017 | Folk | .......................... | F16F 9/16 |
| 2021/0121634 A1* | 4/2021 | Helmer | ............... | A61M 5/2033 |

FOREIGN PATENT DOCUMENTS

| | | |
|---|---|---|
| CN | 217409470 U | 9/2022 |
| EP | 0758255 B1 | 8/2002 |
| JP | H07513 A | 1/1995 |

OTHER PUBLICATIONS

Written Opinion in PCT/CN2023/092040 mailed on Jul. 9, 2023, 6 pages.

* cited by examiner

FIG.. 4

BOOSTER MECHANISMS SUITABLE FOR LIQUID CONTAINERS

CROSS-REFERENCE TO RELATED APPLICATIONS

This application is a Continuation-in-part of International Application No. PCT/CN2023/092040, filed on May 4, 2023, which claims priority to Chinese Application No. 202221126753.3, filed on May 11, 2022, the entire contents of each which are hereby incorporated by reference.

TECHNICAL FIELD

The present disclosure relates to a field of booster mechanisms, and in particular, to booster mechanisms suitable for a liquid container.

BACKGROUND

Currently, in order to facilitate a user realizing an independent and convenient self-administration medication, a self-administration system or a self-administration device has become relatively popular. A tail end and an outer side of a movable assembly outwardly expand and deform obviously when a conventional structure is currently used for striking, which increases a force of friction between the movable assembly and an external contact surface, affects a smooth progress of the movable assembly, and is likely to result in a plurality of defects in use such as an injection failure or an incomplete injection.

Therefore, it is desirable to provide booster mechanisms suitable for a liquid container that can effectively reduce the force of friction during an injection process, so that the injection can be completely carried out.

SUMMARY

One of the embodiments of the present disclosure provides a booster mechanism suitable for a liquid container. The booster mechanism suitable for a liquid container may include a liquid storage assembly. A tail end of the liquid storage assembly may be provided with a strike space. The strike space may be provided with a movable assembly. The movable assembly may be capable of performing an axial movement along the strike space. A tail end of the movable assembly may be provided with a booster assembly, wherein a front end of the booster assembly is provided with a deformation trigger assembly; and a deformation space, wherein a deformation gap is between the deformation space and the deformation trigger assembly.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, where like reference numerals represent similar structures throughout the several views of the drawings, and where.

Figure 1:
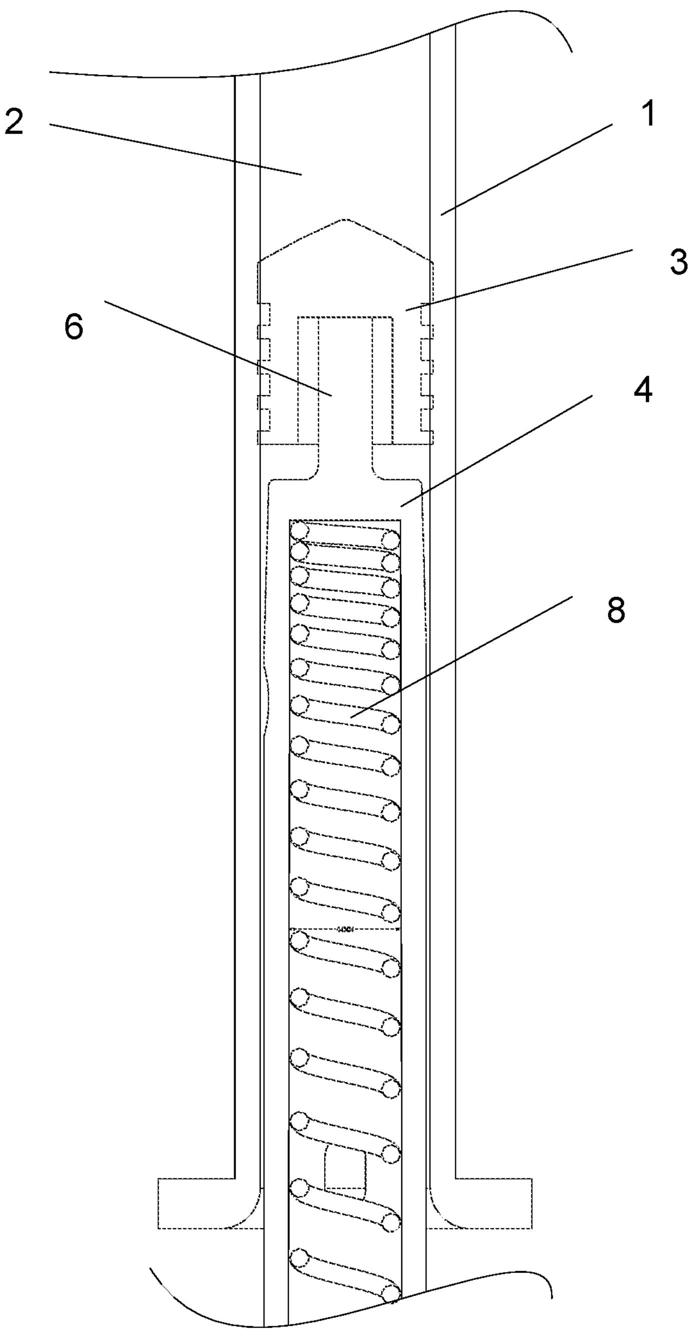
FIG. 1 is a schematic diagram illustrating an exemplary overall structure of a booster mechanism suitable for a liquid container according to some embodiments of the present disclosure.

In the figure, 1, liquid storage assembly, 2, strike space, 3, movable assembly, 3-1, groove, 4, booster assembly, 5, deformation space, 6, deformation trigger assembly, 6-1, protrusion, 7, airtight ring, 71, sealing reinforcement ring, 8, spring, 9, thrust amplification member, 9-1, press slider, 9-2, liquid channel, 9-21, connecting member, 9-3, thrust slider, 10, reminder device, 10-1, card member, and 10-2, shrapnel.

DETAILED DESCRIPTIONS

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing.

Figure 2:
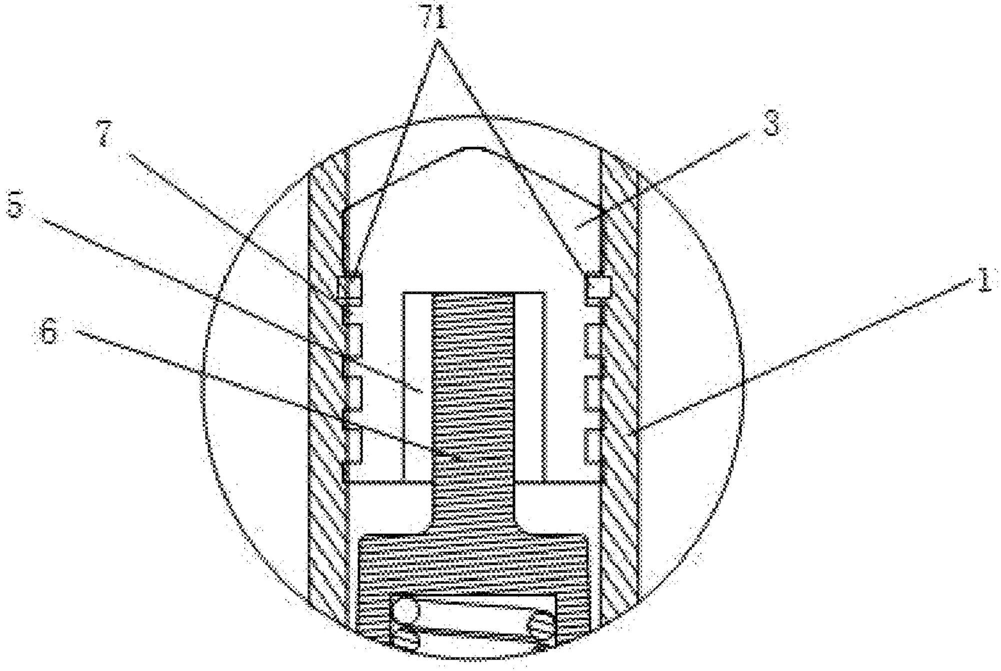
FIG. 2 is a schematic diagram illustrating an exemplary contact between a deformation trigger assembly and a movable assembly when a booster mechanism is in a standby state according to some embodiments of the present disclosure.
Figure 3:
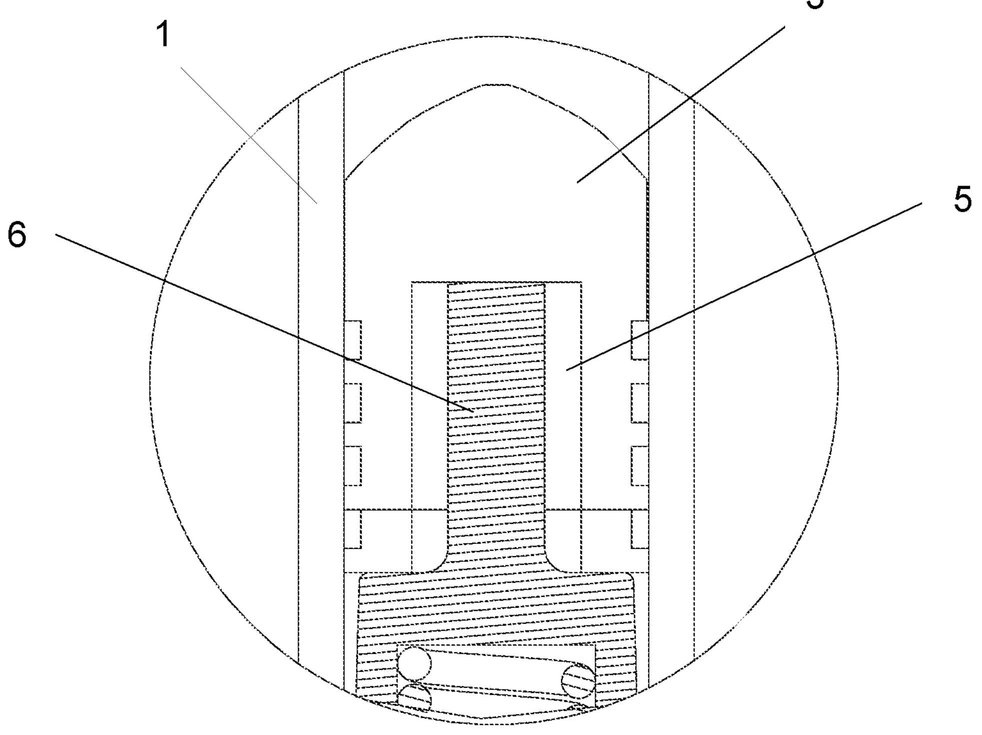
FIG. 3 is a schematic diagram illustrating an exemplary contact between a deformation trigger assembly and a movable assembly when a booster mechanism is in a striking state according to some embodiments of the present disclosure.

FIG. 1 is a schematic diagram illustrating an exemplary overall structure of a booster mechanism suitable for a liquid container according to some embodiments of the present disclosure. FIG. 2 is a schematic diagram illustrating an exemplary contact between a deformation trigger assembly and a movable assembly when a booster mechanism is in a standby state according to some embodiments of the present disclosure. FIG. 3 is a schematic diagram illustrating an exemplary contact between a deformation trigger assembly and a movable assembly when a booster mechanism is in a striking state according to some embodiments of the present disclosure.

As shown in FIG. 1 to FIG. 3, in some embodiments, the booster mechanism suitable for a liquid container may include a liquid storage assembly 1. A tail end of the liquid storage assembly 1 may be provided with a strike space 2. The strike space 2 may be provided with a movable assembly 3.

The liquid storage assembly 1 refers to a container for storing a liquid. The strike space 2 refers to a spatial structure configured to dispose the movable assembly 3. In some embodiments, the movable assembly 3 may be capable of performing an axial movement along the strike space 2. In some embodiments, a tail end of the movable assembly 3 may be provided with a booster assembly 4 and a deformation space 5. The booster assembly 4 refers to an assembly configured to apply a boosting force to the movable assembly 3. The deformation space 5 refers to a space configured to accommodate a deformation trigger assembly 6.

The deformation trigger assembly 6 refers to an assembly configured to trigger the movable assembly 3 to deform. In some embodiments, a front end of the booster assembly 4 may be provided with the deformation trigger assembly 6. For example, the deformation trigger assembly 6 may be a portion extending from the front end of the booster assembly 4. As another example, the deformation trigger assembly 6 may be disposed at the front end of the booster assembly 4 through a fixed connection (e.g. a welding connection). In some embodiments, the deformation trigger assembly 6 may deform the movable assembly 3 by applying a force. In some embodiments, a deformation gap may be between the deformation space 5 and the deformation trigger assembly 6. The deformation gap refers to a gap configured to allow the movable assembly 3 to undergo a shrinkage deformation. As shown in FIG. 1 to FIG. 3, since the deformation gap overlaps with the deformation space 5 (i.e., the deformation gap is a portion of the deformation space 5), an outer side wall of the deformation trigger assembly 6 may not contact an inner side wall of the deformation space 5. More descriptions regarding the deformation trigger assembly 6 and the shrinkage deformation may be found below.

In some embodiments, the booster mechanism may include the standby state. When the booster mechanism is in the standby state, there may be an interference fit between an outer side of the movable assembly and a side wall of the strike space, which may ensure proper airtightness in the strike space 2 and no liquid leakage. The standby state refers to a state where the booster mechanism is not subjected to a force applied by an external environment (e.g., a user) to cause the booster mechanism to perform an injection.

In some embodiments, the booster mechanism may include the striking state. When the booster mechanism is in the striking state, a head end of the movable assembly 3 may have a convex deformation, and there may be no interference fit between the outer side of the movable assembly 3 and the side wall of the strike space 2. The striking state refers to a state where the booster mechanism is subjected to the force applied by the external environment and is performing the injection. As shown in FIG. 3, when the booster mechanism is in the striking state, an end of the deformation trigger assembly 6 may apply a continuous contact force to an inner top of the deformation space 5, so that the head end of the movable assembly 3 may have the convex deformation, thereby eliminating the interference fit between the outer side of the movable assembly 3 and the side wall of the strike space 2. Understandably, the convex deformation of the head end of the movable assembly 3 may cause a periphery of the movable assembly 3 to have the shrinkage deformation, i.e., the convex deformation may cause the movable assembly 3 to have a proper concave (i.e., shrinkage deformation) in a direction facing the deformation gap. In some embodiments, the shrinkage deformation may reduce a force of friction between the movable assembly 3 and the side wall of the strike space 2, thereby making the movable assembly 3 to move forward smoothly when subjected to the force to realize a supply injection of the liquid.

In some embodiments, a connection between the deformation trigger assembly and the front end of the booster assembly may be provided with a circular arc concave chamfer, which may improve a firmness of the connection, so that when the deformation trigger assembly 6 applies the force to the movable assembly 3, there may be no abnormal force on the movable assembly 3 caused by other stresses that may be brought by an impact of striking.

In some embodiments, the deformation space 5 may include a cylindrical groove. The deformation trigger assembly 6 may include a cylindrical convex bar. A diameter of the cylindrical convex bar may be smaller than a diameter of the cylindrical groove, so that the deformation gap may be formed between the trigger assembly 6 and the deformation space 5 and a smoothness of the deformation trigger assembly 6 may be improved when the deformation trigger assembly 6 applies the force to the movable assembly 3. In some embodiments, the diameter of the cylindrical convex bar may be smaller than the diameter of the cylindrical groove, so that when the head end of the movable assembly 3 has the convex deformation, the movable assembly 3 may have a proper deformation space 5, thereby ensuring that the outer side of the movable assembly 3 may smoothly deform inwardly (i.e., the shrinkage deformation). In some embodiments, the deformation space 5 may also include groove structures in other shapes, such as a frustum of a cone-shaped groove, or a frustum of a prism-shaped groove. In some embodiments, the deformation trigger assembly 6 may also include other protrusion structures in other shapes, such as a frustum of a cone-shaped convex bar, or a frustum of a prism-shaped convex bar.

As shown in FIG. 3, in some embodiments, a plurality of airtight rings 7 may be distributed on the outer side of the movable assembly 3. When the booster mechanism is in the standby state, the plurality of airtight rings 7 may contact the side wall of the strike space 2, which may ensure airtightness of the strike space 2 when the booster mechanism is in the standby state.

In some embodiments, the plurality of airtight rings 7 may be distributed on the outer side of the movable assembly 3, so that when the booster mechanism is in the striking state, the booster mechanism may simultaneously make the movable assembly 3 move smoothly forward along the strike space 2 and maintain proper airtightness in the strike space 2, thereby preventing the liquid leakage. In some embodiments, the plurality of airtight rings 7 may be distributed on the outer side of the movable assembly 3 in a plurality of distribution manners. For example, the plurality of airtight rings 7 may be distributed at an equal interval distance, an equidistant interval distance, etc.

In some embodiments, at least one of the plurality of airtight rings 7 may be trapezoidal or V-shaped, i.e., a cross-section of the at least one of the plurality of airtight rings 7 may be trapezoidal or V-shaped. The plurality of trapezoidal or V-shaped airtight rings 7 may contact the side wall of the strike space 2, which may effectively reduce a contact area between the plurality of airtight rings 7 and the side wall of the strike space 2, thereby reducing the force of friction between the movable assembly 3 and the side wall of the strike space 2, so that the movable assembly 3 may smoothly move forward to realize the injection of the liquid.

As shown in FIG. 2, in some embodiments, the booster mechanism may include a sealing reinforcement ring 71. The sealing reinforcement ring 71 may be sleeved on the movable assembly 3, and an elasticity modulus of the sealing reinforcement ring 71 may be greater than an elasticity modulus of the movable assembly 3.

The sealing reinforcement ring 71 refers to a structure used to reinforce the airtightness of the strike space 2 when the booster mechanism is in the striking state. For example, the sealing reinforcement ring 71 may include an O-shaped rubber ring, a silicone ring, etc.

The elasticity modulus refers to a physical quantity used to describe a degree of deformation of a material when the material is subjected to stress. In some embodiments, when the booster mechanism is subjected to the force applied by the external environment, i.e., in the striking state, the deformation trigger assembly 6 may contact and apply the force to the inner top of the deformation space 5, so that the movable assembly 3 and the sealing reinforcement ring 71 sleeved on the movable assembly 3 may deform. Since the elasticity modulus of the sealing reinforcement ring 71 is greater than the elasticity modulus of the movable assembly 3, a degree of deformation of the sealing reinforcement ring 71 may be smaller than a degree of deformation of the movable assembly 3.

In some embodiments, the sealing reinforcement ring 71 may be sleeved on the movable assembly 3 and the elasticity modulus of the sealing reinforcement ring 71 may be greater than the elasticity modulus of the movable assembly 3, so that when the booster mechanism is in the striking state, and when the movable assembly 3 deforms at the same time, the sealing reinforcement ring 71 may maintain an original shape or deform only to a relatively small degree, thereby improving the airtightness inside the booster mechanism.

As shown in FIG. 1, in some embodiments, the booster assembly 4 may be provided with a spring 8. The spring 8 may apply the force for striking by cooperating with other assemblies of the booster mechanism, thereby ensuring that the booster mechanism may inject the liquid smoothly when the booster mechanism is in the striking state. Exemplarily, when the booster mechanism is in the standby state, the spring 8 may be in a compression state, and at this time, the spring 8 may store a preload. When the standby state of the booster mechanism is converted to the striking state, the spring 8 in the compression state may release the stored preload, thereby driving the deformation trigger assembly 6 to apply the force to the movable assembly 3 for striking and smoothly injecting the liquid. More descriptions regarding the deformation trigger assembly 6 may be found above.

In some embodiments, an outer side of the booster assembly 4 may be provided with a press slider (not shown). One end of the spring 8 may be connected to the press slider, and another end of the spring 8 may be connected to the movable assembly 3.

The press slider refers to a member used to connect the spring 8 to the booster assembly 4. In some embodiments, the two ends of the spring 8 may be respectively connected to the press slider and the movable assembly 3 through a plurality of connection manners. Exemplarily, the press slider may be provided as a snap ring. One end of the spring 8 may be hooked into the snap ring for the purpose of connecting the press slider, and another end of the spring 8 may be directly welded to the movable assembly 3. In some embodiments, when the booster mechanism is in the striking state, the booster assembly 4 may push and squeeze along a direction y towards the movable assembly 3, and as the booster assembly 4 is close to the movable assembly 3, the spring 8 may be gradually compressed and store the preload. When the booster mechanism completes the injection of the liquid, and as the striking state is removed, a compressed spring 8 may release the preload and rebound, so that the booster assembly 4 may return to an initial position, thereby ensuring that the booster mechanism may re-inject the liquid.

In some embodiments, the two ends of the spring 8 may be respectively connected to the press slider and the movable assembly 3, so that the booster assembly 4 may automatically return to the initial position after completing the injection of the liquid, and convenience of the booster mechanism to inject the liquid can be improved.

In some embodiments, a working principle of the booster mechanism is as follows.

When the booster mechanism is in the standby state, there may be the interference fit between the outer side of the movable assembly 3 and the side wall of the strike space 2, or the outer side of the movable assembly 3 may be in at least close contact with the side wall of the strike space 2, so that it may be possible to ensure that there is the deformation gap distributed between the deformation trigger assembly 6 and the deformation space 5.

When the booster mechanism is in the striking state, and as the booster assembly 4 moves forward, the deformation trigger assembly 6 may begin to resist the inner top of the deformation space 5 in the movable assembly 3, and at this time, the movable assembly 3 may begin to be subjected to the continuous striking force applied by the deformation trigger assembly 6. As the booster assembly 4 continues to move forward, the movable assembly 3 may gradually move forward in synchronization with the booster assembly 4. In addition, the movable assembly 3 may be subjected to the force and deform, i.e., the head end of the movable assembly 3 may be subjected to the continuous striking force applied by the deformation trigger assembly 6 and generate the convex deformation. The convex deformation may cause the shrinkage deformation around the movable assembly 3, and the shrinkage deformation may reduce the force of friction between the movable assembly 3 and the side wall of the strike space 2, which may ensure that the movable assembly 3 may move forward smoothly by the force and satisfy the supply injection of the liquid. During this process, the booster assembly 4 may continue to move forward until the tail end of the movable assembly 3 abuts an upper end surface of the booster assembly 4.

In some embodiments, the liquid storage assembly may also be replaced with a gas storage assembly to ensure that the booster mechanism may realize the supply injection of gas.

It should be noted that in FIG. 1 and FIG. 2, in order to better represent the interference fit, the plurality of airtight rings 7 may partially overlapped with the side wall of the strike space 2. At the same time, the convex deformation in FIG. 3 may have a portion of drawing that exaggerates the deformation, which is only used to indicate an existence of a deformation state. Moreover, other portions of the movable assembly 3 may also deform, which is not fully represented in the figure.

In some embodiments of the present disclosure, the booster mechanism in the striking state may reduce the force of friction of the movable assembly 3, so that the movable assembly 3 may move forward smoothly and the supply injection of liquid may be achieved. The overall structure of the booster mechanism is simple and has a good sealing effect, so that there is no liquid leakage during use and storage. In some embodiments of the present disclosure, the booster mechanism may be obtained by performing a simple modification and replacement on the booster assembly 4, so that an original usage habit may not be affected, the implementation cost is low, and the versatility is relatively good.

Figure 4:
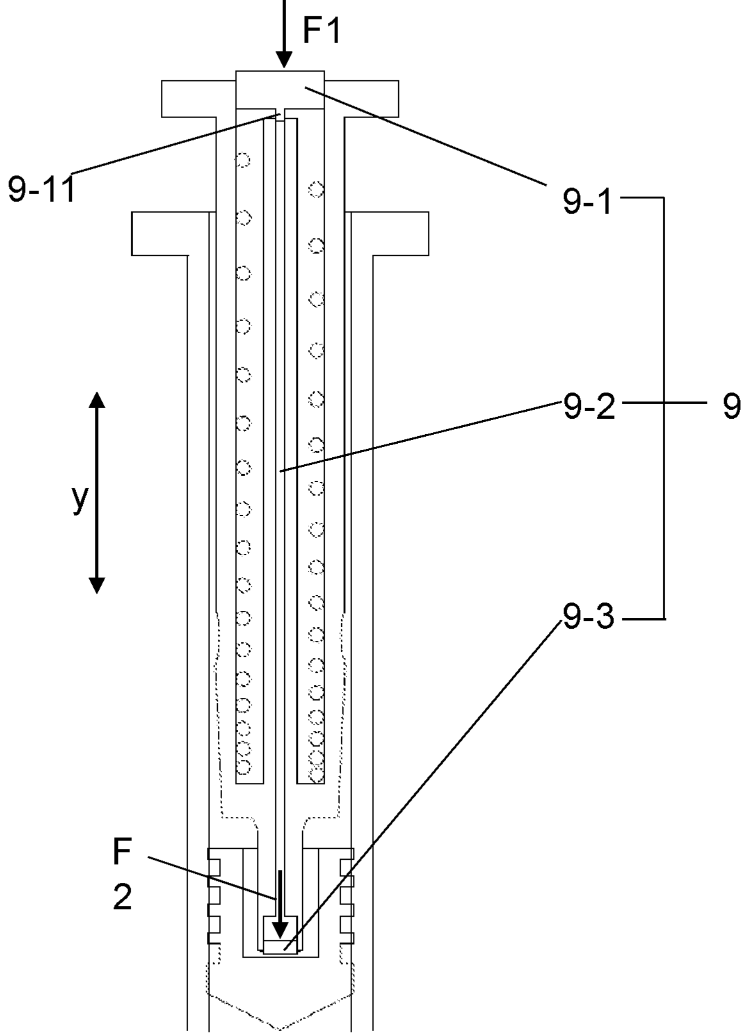
FIG. 4 is a schematic diagram illustrating an exemplary structure of a thrust amplification member according to some embodiments of the present disclosure.

FIG. 4 is a schematic diagram illustrating an exemplary structure of a thrust amplification member according to some embodiments of the present disclosure.

As shown in FIG. 4, in some embodiments, the booster assembly 4 may include a thrust amplification member 9. The thrust amplification member 9 may include a press slider 9-1, a liquid channel 9-2, and a thrust slider 9-3. The liquid channel 9-2 may be disposed between the press slider 9-1 and the thrust slider 9-3, and the liquid channel 9-2 may have a filling liquid.

The thrust amplification member 9 refers to a member used to amplify a thrust applied by a user to the booster assembly 4.

The press slider 9-1 refers to a slider used to apply the thrust (i.e., a press force) by the user.

The liquid channel 9-2 refers to a device that amplifies the thrust applied by the user to the press slider 9-1. In some embodiments, the liquid channel 9-2 may be filled with the filling liquid. The filling liquid refers to a liquid that transmits the thrust applied by the user on the press slider 9-1 to the thrust slider 9-3. For example, the filling liquid may include hydraulic oil, water, and silicone oil.

The thrust slider 9-3 refers to a slider used to push the booster assembly 4. Understandably, since the filling liquid is incompressible, the thrust applied by the user to the press slider 9-1 may be transmitted to the thrust slider 9-3 through the filling liquid contacting the press slider 9-1.

Figure 5:
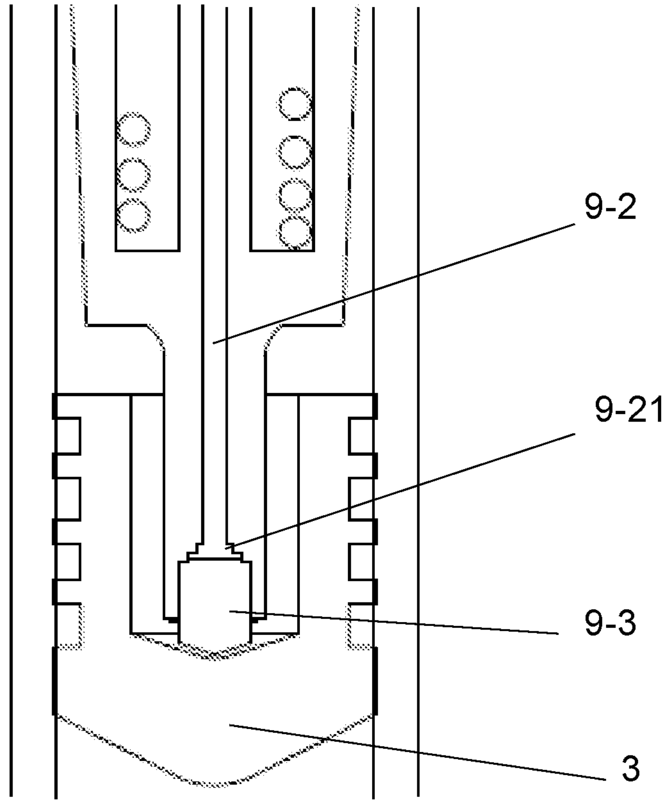
FIG. 5 is a schematic diagram illustrating an exemplary structure of a connecting member according to some embodiments of the present disclosure.

In some embodiments, the press slider 9-1 and the thrust slider 9-3 may be disposed at two ends of the liquid channel 9-2, respectively, along the direction y (as shown in FIG. 5). In some embodiments, the press slider 9-1 and the thrust slider 9-3 may respectively contact the filling liquid along two ends of the direction y. In some embodiments, a contact area between the press slider 9-1 and the filling liquid may be smaller than a contact area between the thrust slider 9-3 and the filling liquid. As shown in FIG. 5, and a force F2 transmitted to the thrust slider 9-3 through the filling liquid may be amplified compared with a thrust F1 applied by the user to the press slider 9-1. According to Pascal's principle, i.e., in an incompressible stationary fluid, if any point is subjected to pressure, the pressure may be instantaneously transmitted to various points of the stationary fluid. Therefore, a pressure generated by the thrust F1 at a contact surface between the press-slide 9-1 and the filling liquid may be equal to a pressure generated by the force F2 at a contact surface between the thrust slider 9-3 and the filling liquid, which may be expressed by the following equation (1).

$$P1 = P2 \tag{1}$$

where P1 denotes the pressure generated by the thrust F1 at the contact surface between the press-slide 9-1 and the filling liquid, and P2 denotes the pressure generated by the force F2 at the contact surface between the thrust slider 9-3 and the filling liquid.

In some embodiments, the pressure P1 and the pressure P2 may be respectively determined by equations (2) and (3) below.

$$P1 = \frac{F1}{A1} \tag{2}$$

$$P2 = \frac{F2}{A2} \tag{3}$$

where A1 denotes the contact area between the press slider 9-1 and the filling liquid, and A2 denotes the contact area between the thrust slider 9-3 and the filling liquid.

In some embodiments, the following equation (4) may be derived from the equations (1), (2), and (3), and the equation (4) is used to describe a relationship between the force F2 on the thrust slider 9-3 and the thrust F1 applied by the user on the press slider 9-1.

$$F2 = \frac{A2}{A1} \cdot F1 \tag{4}$$

In some embodiments, since the contact area A2 between the thrust slider 9-3 and the filling liquid is larger than the contact area A1 between the press slider 9-1 and the filling liquid, it may be seen from the equation (4) that the force F2 transmitted to the thrust slider 9-3 through the filling liquid increases to A2/A1 times the thrust F1 applied by the user to the press slider 9-1.

As shown in FIG. 4, in some embodiments, the press slider 9-1 may include an extension member 9-11. The extension member 9-11 may be disposed within the liquid channel 9-2, and a height of the filling liquid within the liquid channel 9-2 may be related to a length of the extension member 9-11.

The extension member 9-11 refers to a component that extends into the liquid channel 9-2 and directly contacts the filling liquid. In some embodiments, the contact area A1 between the press slider 9-1 and the filling liquid may be a contact area between the extension member 9-11 and the filling liquid. In some embodiments, different press sliders 9-1 may have extension members 9-11 of different lengths. By replacing with the different press sliders 9-1, the extension members 9-11 of different lengths may extend into the liquid channel 9-2 of a corresponding height, i.e., the extension members 9-11 may occupy a space of a same length (i.e., height) of the liquid channel 9-2. At this time, the height of the filling liquid within the liquid channel 9-2 may accordingly decrease, i.e. the longer the length of the extension member 9-11 is, the smaller the height of the filling liquid within the liquid channel may be. It should be noted that the booster mechanism is approximately in a vertical position when used. Therefore, when the height of the filling liquid within the liquid channel 9-2 accordingly decreases, a pressure on the thrust slider 9-3 at a lower end may also decrease accordingly. Therefore, in some embodiments, the length of the liquid channel 9-2 occupied by the extension member 9-11 may be adjusted by adjusting the length of the extension member 9-11, which may change the height of the filling liquid and the pressure of the thrust slider 9-3, so that the thrust applied by the user to the press slider 9-1 may be amplified to different degrees, i.e., the thrust slider 9-3 may be subjected to not only the pressure generated by the force F2 but also a liquid pressure generated by the filling liquid. In some embodiments, the pressure to which the thrust slider 9-3 is actually subjected may be expressed by the following equation (5).

$$P3 = \rho gh + P2 \tag{5}$$

where P3 denotes the pressure to which the thrust slider 9-3 is actually subjected, p denotes a density of the filling liquid, g denotes a gravitational acceleration, and h denotes the height of the filling liquid within the liquid channel 9-2. At this time, the pressure to which the thrust slider 9-3 is actually subjected may generate an actual thrust on the thrust slider 9-3, and a relationship between the actual thrust and the pressure to which the thrust slider 9-3 is actually subjected may be expressed by the following equation (6).

$$P3 = F3 \cdot A2 \tag{6}$$

F3 denotes the actual thrust to which thrust slider 9-3 is subjected. According to the equation (1), the equation (2), the equation (5) and the equation (6), the following equation (7) may be derived, and the equation (7) may be used to describe the actual thrust to which the thrust slider 9-3 is subjected.

$$F3 = \frac{A2}{A1} \cdot F1 + \frac{\rho g}{A1} \cdot h \tag{7}$$

According to the equation (7), the height h of the filling liquid within the liquid channel 9-2 may increase the actual thrust to which the thrust slider 9-3 is subjected, i.e., the greater the height of the filling liquid within the liquid channel 9-2 is, the more the force transmitted to the thrust slider 9-3 through the filling liquid based on the thrust applied by the user to the press slider 9-1 may increase.

In some embodiments of the present disclosure, the height of the filling liquid within the liquid channel 9-2 may be adjusted by choosing the extension members 9-11 of different lengths, so that the force applied by the user to the booster mechanism may be further increased and amplified, thereby ensuring that the user may control an injection effect of the liquid accurately.

FIG. 5 is a schematic diagram illustrating an exemplary structure of a connecting member according to some embodiments of the present disclosure.

As shown in FIG. 5, in some embodiments, the liquid channel 9-2 may be provided with a connecting member 9-21. The connecting member 9-21 may be in a shape of a step, and the thrust slider 9-3 may be detachably connected to the connecting member 9-21.

The connecting member 9-21 refers to a member that connects the liquid channel 9-2 to the thrust slider 9-3. In some embodiments, the connecting member 9-21 may be disposed at one end of the liquid channel 9-2 along the direction y through a plurality of connection manners (e.g., the welding connection, or an adhesive connection). The connecting member 9-21 may include a step of different rungs, and the thrust slider 9-3 may be detachably connected to the connecting member 9-21. For example, a detachable connection may be a snapping connection. In some embodiments, thrust sliders 9-3 of different sizes may be respectively detachably connected to the step of different rungs. The contact area A2 between the thrust sliders 9-3 and the filling liquid may be changed by replacing the thrust sliders 9-3 of different sizes, so that the force F2 on the thrust sliders 9-3 may be increased to different degrees. Exemplarily, the connecting member may include a step of three rungs. The step of the three rungs may be connected to three kinds of thrust sliders 9-3 with gradually increasing sizes in sequence along the direction y from top to bottom. The contact areas A2 between the three kinds of thrust sliders 9-3 and the filling liquid may be 5 times, 10 times, and 15 times the contact area A1 between the press slider 9-1 and the filling liquid, respectively. When the three kinds of thrust sliders 9-3 are respectively connected to the step corresponding to the connecting member, the force F2 transmitted to the thrust sliders 9-3 through the filling liquid may respectively increase to 5 times, 10 times, and 15 times the thrust applied by the user to the press slider 9-1. In some embodiments, when the liquid channel 9-2 is not provided with the connecting member 9-21, the thrust sliders 9-3 of the different sizes may also be replaced in various ways. For example, the thrust sliders 9-3 of the different sizes may be replaced through a threaded connection, a magnet connection, etc.

In some embodiments, a thickness of the head end of the movable assembly 3 may be set as required. The thickness of the head end of the movable assembly 3 may be negatively correlated with a deformation degree of the convex deformation occurring at the head end, and the thickness of the head end of the movable assembly 3 may be negatively correlated with a deformation degree of the shrinkage deformation occurring at a periphery of the head end of the movable assembly 3. It may be understood that when the force exerted on the movable assembly 3 (i.e., the inner top of the deformation space 5 described above) by the thrust slider 9-3 is constant, the greater the thickness of the head end of the movable assembly 3 disposed in the strike space 2 is, the smaller the deformation degree of the convex deformation occurring at the head end of the movable assembly 3 may be, and the smaller the deformation degree of the shrinkage deformation occurring at the periphery of the movable assembly 3. More descriptions regarding the convex deformation and the shrinkage deformation may be found above.

In some embodiments, the thrust sliders 9-3 of different sizes may be set to match the movable assemblies 3 with the head ends of different thicknesses, which may effectively expand the thrust (i.e., the thrust F1 applied by the user) to different degrees, so that the booster mechanism may achieve an effect of a plurality of injection requirements by merely replacing the thrust sliders 9-3 and the movable assemblies 3. For example, a movable assembly 3 with a head end of a relatively small thickness may be disposed in the strike space 2, and a relatively small thrust slider 9-3 may be disposed, which may make the contact area A2 between the relatively small thrust slider 9-3 and the filling liquid relatively small, so that the movable assembly 3 may have a maximum convex deformation and a maximum shrinkage deformation, thereby ensuring that the booster mechanism achieves a relatively large injection speed.

In some embodiments of the present disclosure, the contact area between the press slider 9-1 and the filling liquid in the liquid channel 9-2 may be different from the contact area between the thrust slider 9-3 and the filling liquid in the liquid channel 9-2, so that the force applied to the press slider 9-1 by the user may be amplified at the thrust slider 9-3, thereby effectively promoting deformation (including the convex deformation and shrinkage deformation) of the movable assembly 3.

Figure 6A:
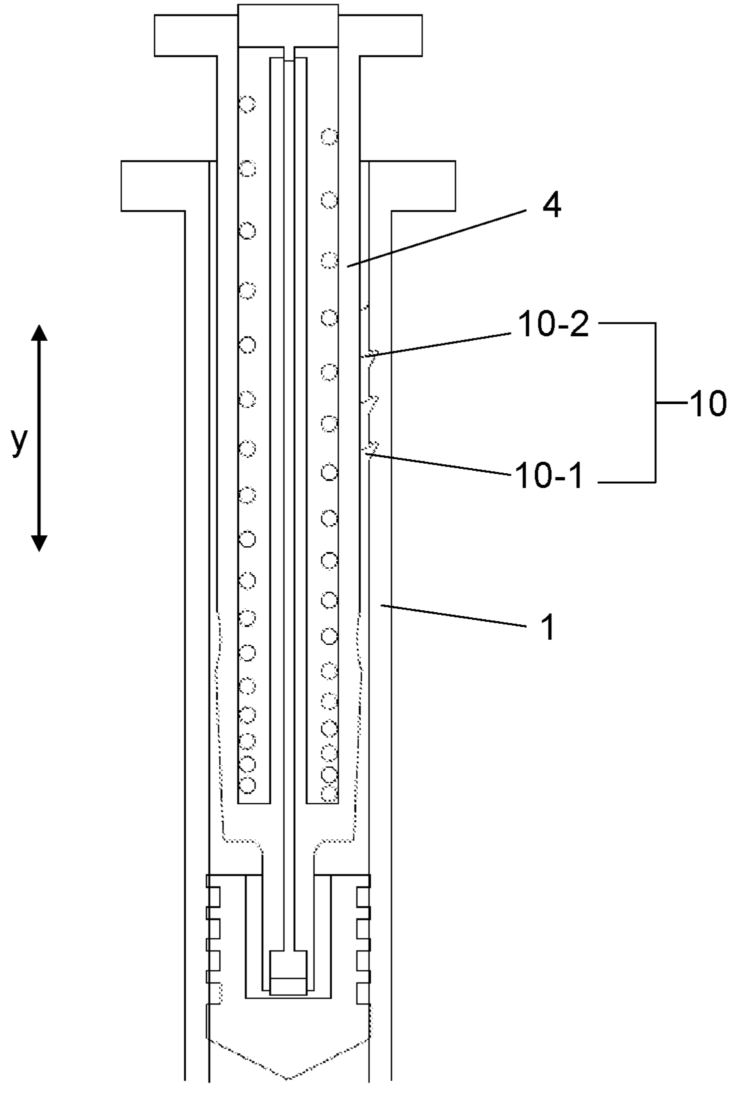
FIG. 6A is a schematic diagram I illustrating an exemplary structure of a reminder device according to some embodiments of the present disclosure.
Figure 6B:
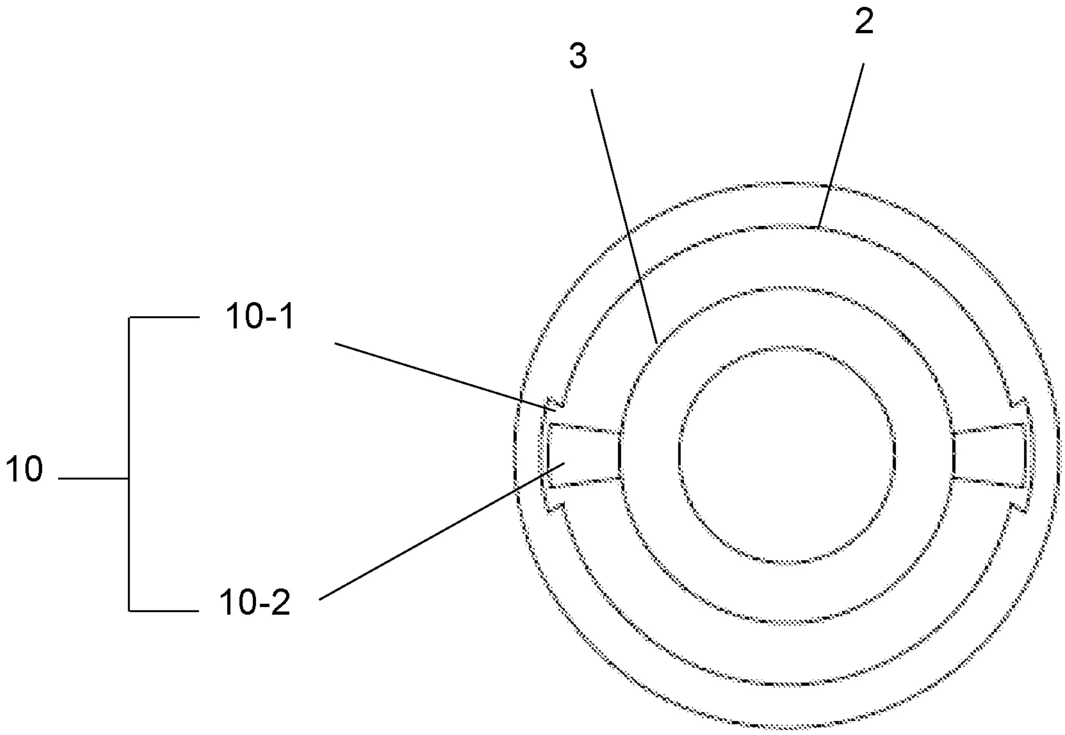
FIG. 6B is a schematic diagram II illustrating an exemplary structure of a reminder device according to some embodiments of the present disclosure.
Figure 6C:
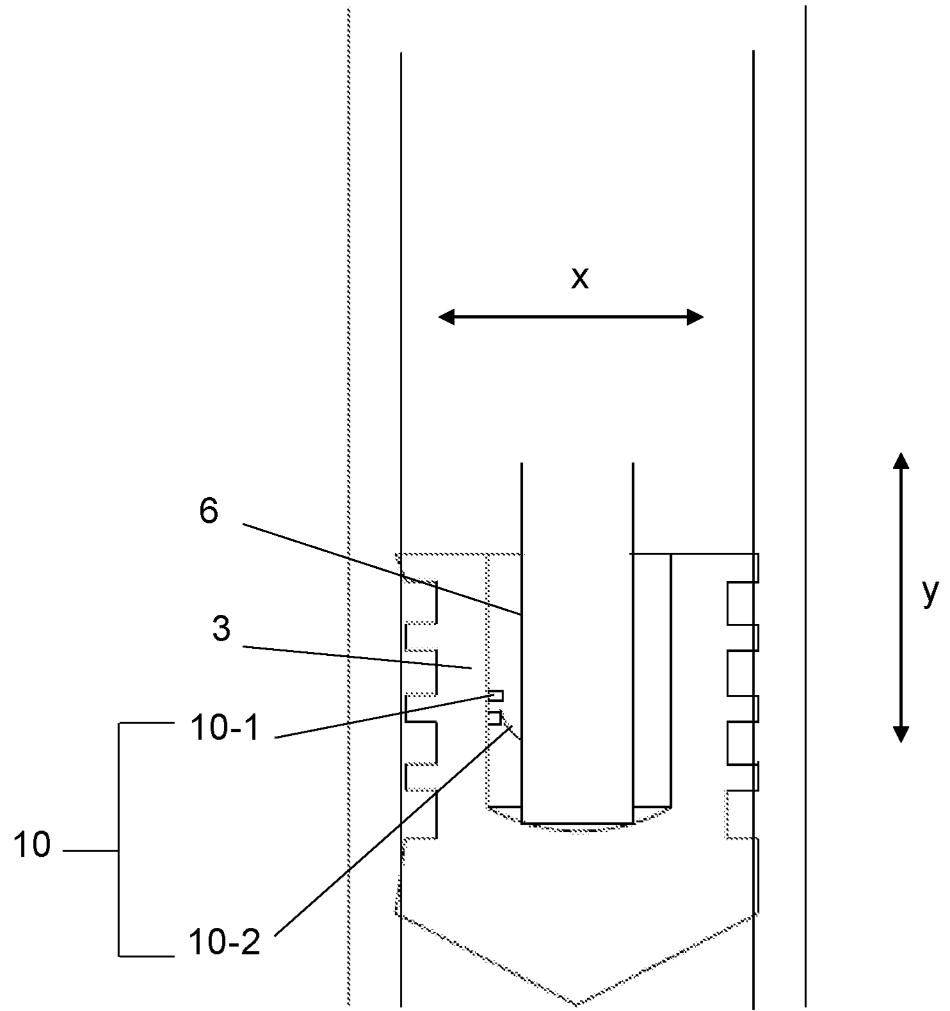
FIG. 6C is a schematic diagram III illustrating an exemplary structure of a reminder device according to some embodiments of the present disclosure.

FIG. 6A is a schematic diagram I illustrating an exemplary structure of a reminder device according to some embodiments of the present disclosure. FIG. 6B is an exemplary schematic diagram II illustrating a structure of a reminder device according to some embodiments of the present disclosure. FIG. 6C is a schematic diagram III illustrating an exemplary structure of a reminder device according to some embodiments of the present disclosure.

As shown in FIG. 6A to FIG. 6C, in some embodiments, the booster mechanism may include a reminder device 10. The reminder device 10 may include card members 10-1 and a shrapnel 10-2. When the booster mechanism is in a striking state, the card members 10-1 and the shrapnel 10-2 may contact to make a sound.

As shown in FIG. 6A, in some embodiments, the card members 10-1 may be disposed on an inner side of the liquid storage assembly 1, and the shrapnel 10-2 may be disposed on an outer side of the movable assembly 3. As shown in FIG. 6B, in some embodiments, the card members 10-1 may be disposed on the inner side of the liquid storage assembly 1, and the shrapnel 10-2 may be disposed on an outer side of the booster assembly 4.

The reminder device 10 refers to a device used to remind the user of a dose of liquid injected by the booster mechanism. The card members 10-1 and the shrapnel 10-2 refer to structures used to cooperate with each other to make the sound to remind the user of the dose of injected liquid. In some embodiments, at least one of the card members 10-1 may be grooved and the shrapnel 10-2 may be a sheet-shaped structure. For example, the at least one of the card member 10-1 may include a curved groove, a square groove, etc., and the shrapnel 10-2 may include a sheet-shaped hard plastic or metal, etc. In some embodiments, the card members 10-1 may be disposed at an equal distance along the direction y on the inner side of the liquid storage assembly 1, and at this time, groove depths of the card members 10-1 may be equal. When the booster mechanism is in the striking state, the booster assembly 4 may push the liquid along the direction y for performing the injection, and at this time, the shrapnel 10-2 may be snapped into the card members 10-1 to remind the user of the dose of injected liquid and an injection speed by making the sound (e.g., a clicking sound). For example, the greater the count of times the sound is made, the further the distance of the booster assembly 4 along the direction y may be, i.e. the greater the dose of liquid injected by the booster mechanism may be. As another example, the higher the frequency of the sound is made, the larger the injection speed may be.

In some embodiments, the card members 10-1 may be disposed at unequal interval distances along the direction y on the inner side of the liquid storage assembly 1, and at this time, the groove depths of the card members 10-1 may be not equal. For example, a distance between a first card member 10-1 and a second card member 10-1 may be greater than a distance between the second card member 10-1 and a third card member 10-1. The distance between the second card member 10-1 and the third card member 10-1 may be greater than a distance between the third card member 10-1 and a fourth card member 10-1. At this time, groove depths of the first card member 10-1 to the fourth card member 10-1 may gradually decrease, so that when the booster assembly 4 is pushed along the direction y, the sound made in turn may gradually become quiet when the shrapnel 10-2 is snapped into the card members 10-1 to remind the user that the dose of injected liquid gradually decreases.

In some embodiments, the booster assembly 4 may drive the shrapnel 10-2 to deviate from positions of the card members 10-1 by being rotated within the strike space 2, so that the booster assembly 4 may push the liquid along the direction y, and the shrapnel 10-2 may not be snapped into the card members 10-1, thereby removing the sound of the booster mechanism when injecting the liquid to remind a user of a pushing distance (i.e., the dose of the injected liquid) of the booster assembly 4 and avoiding interference to the user. In some embodiments, the shrapnel 10-2 may be derived to deviate from the positions of the card members 10-1 by rotating the booster assembly 4, so that the booster assembly 4 may be pulled along an opposite direction of pushing the liquid for injection, and the booster mechanism may extract the liquid.

As shown in FIG. 6C, in some embodiments, a shape of the at least one of the card members 10-1 may further include a shape of a convex bar. The card members 10-1 may be disposed on an inner side of the movable assembly 3, and the shrapnel 10-2 may be disposed on the deformation trigger assembly 6. In some embodiments, the card members 10-1 and the shrapnel 10-2 may be made of metal (e.g., copper, or iron) to improve the sound made when the card members 10-1 and the shrapnel 10-2 contact. Exemplarily, the inner side of the movable assembly 3 may be provided with 2 card members 10-1, and the booster assembly 4 may be provided with a metal shrapnel 10-2. When the booster mechanism is in a standby state, the shrapnel 10-2 and an upper card member 10-1 may contact. When the standby state of the booster mechanism is converted into the striking state, the booster assembly 4 may drive the deformation trigger assembly 6 to squeeze the movable assembly 3. At this time, the movable assembly 3 may deform, and the shrapnel 10-2 may detach from the upper card member 10-1 and contact a lower card member 10-1 to make the sound.

In some embodiments, the sound made by a contact between the card members 10-1 and the shrapnel 10-2 may be configured to determine the deformation degree that the movable assembly 3 undergoes. In some embodiments, the plurality of card members 10-1 may be disposed on the inner side of the movable assembly 3, and lengths of the plurality of card members 10-1 (i.e., the lengths of the plurality of card members 10-1 along a direction x shown in FIG. 6C) may decrease sequentially from top to bottom. From top to bottom refers to a movement direction of the booster assembly 4 when pushing the liquid for injection. When the standby state of the booster mechanism is converted into the striking state, the booster assembly 4 may drive the shrapnel 10-2 to contact the card members 10-1 in sequence from top to bottom to make the sound. The greater the count of times the sound is made, the greater the deformation degree of the movable assembly 3 may undergo. Exemplarily, the inner side of the movable assembly 3 may be provided with three card members 10-1 with lengths of a, b, and c, respectively, from top to bottom, where $a>b>c$. When one of the three card members 10-1 and the shrapnel 10-2 contact to make a first sound, the movable assembly 3 may be squeezed by the booster assembly 4 and deform (i.e., shrinkage deformation) by a distance of $a-b$ along the direction x. Similarly, when one of the three card members 10-1 and the shrapnel 10-2 contact to make a second sound, the movable assembly 3 may deform (i.e., the shrinkage deformation) by a distance of $a-c$ along the direction x. Understandably, the deformation degree of the movable assembly 3 along the direction x may be configured to indicate a magnitude of a force of friction to which the movable assembly 3 is subjected, i.e., the greater the deformation degree of the movable assembly 3 along the direction x is, the smaller the force of friction between the movable assembly 3 and the side wall of the strike space 2.

In some embodiments, the sound made by the contact between the card members 10-1 and the shrapnel 10-2 may be configured to determine replacement of the press slider 9-1 or the thrust slider 9-2. Exemplarily, when the injected liquid of the booster mechanism is replaced, a viscosity of the liquid may increase. When an original thrust is applied to the press slider 9-1, the injection speed when the injected liquid is not been replaced may not be achieved. At this time, a larger thrust may be applied to the press slider 9-1, and the press slider 9-1 or the thrust slider 9-2 may be replaced according to the count of times that the sound is made by the contact between the at least one of the card members 10-1 and the shrapnel 10-2. For example, before the injected liquid of the booster mechanism is replaced, when a thrust applied to the press slider 9-1 is 1N, the card members 10-1 and the shrapnel 10-2 may contact to make the sound 2 times. After the injected liquid of the booster mechanism is replaced, if only when the thrust applied to the press slider 9-1 is 2N, the card members 10-1 and the shrapnel 10-2 may contact to make the sound 2 times, the press slider 9-1 or the thrust slider 9-2 may be replaced, and the replaced press slider 9-1 may make a height of the filling liquid within the liquid channel 9-2 increase. The specific increased height may be calculated through the equation (7) above, which is not specifically calculated herein. A contact area between the thrust slider 9-2 and the filling liquid after replacement may be more than twice a contact area between the thrust slider 9-2 and the filling liquid before replacement. More descriptions regarding the press slider 9-1 or the thrust slider 9-2 may be found in FIG. 4 and FIG. 5 and the related descriptions thereof.

In some embodiments, the card members 10-1 and the shrapnel 10-2 may contact to make the sound, which may remind the user of the dose of the liquid injected by the booster mechanism promptly to ensure that a proper dose of the liquid is injected. In addition, the sound made by the contact between the card members 10-1 and the shrapnel 10-2 may be configured to assist the user in replacing the press slider 9-1 or the thrust slider 9-2 to ensure that the booster mechanism has a suitable injection speed, which may effectively prevent the movable assembly 3 from generating an excessive deformation or even causing a permanent deformation, thereby avoiding affecting a service life and a sealing of the booster mechanism.

Figure 7:
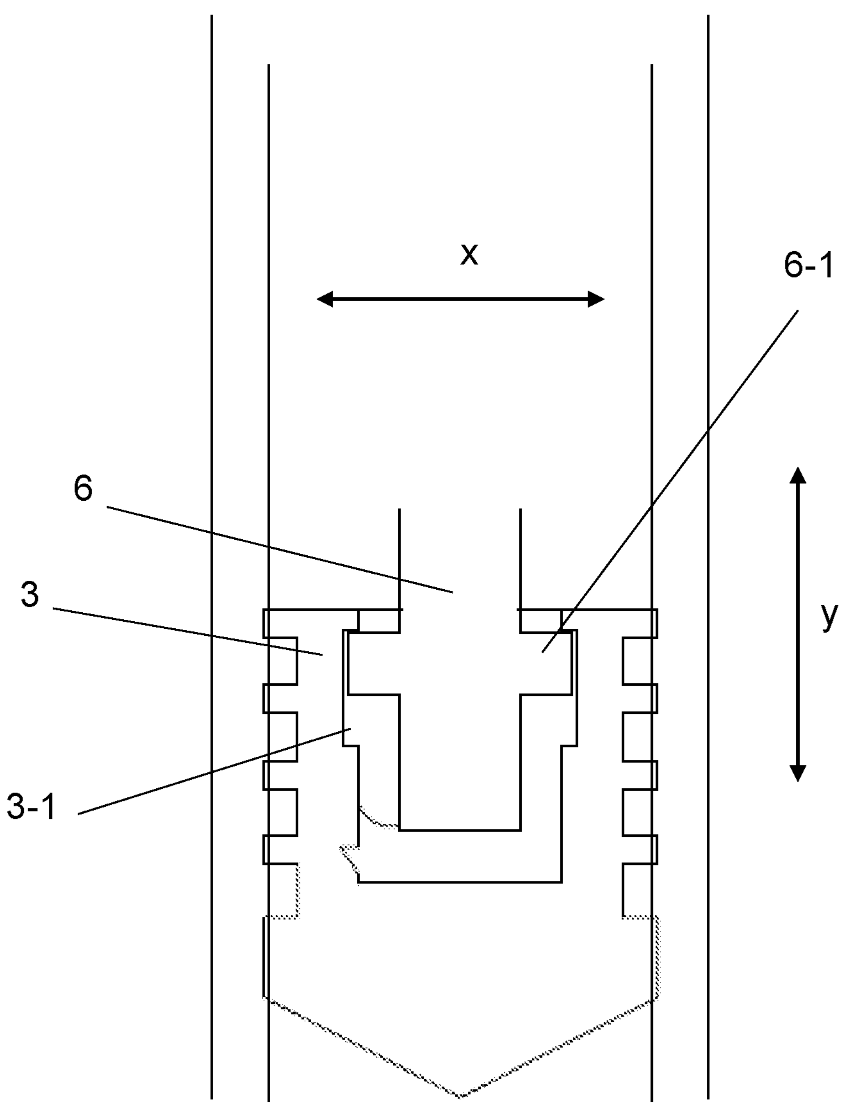
FIG. 7 is a schematic diagram illustrating an exemplary structure of a protrusion and a groove according to some embodiments of the present disclosure.

FIG. 7 is a schematic diagram illustrating an exemplary structure of a protrusion and a groove according to some embodiments of the present disclosure.

As shown in FIG. 7, in some embodiments, the deformation trigger assembly 6 may include a protrusion 6-1. The movable assembly 3 may include a groove 3-1. The protrusion 6-1 may be slidably disposed in the groove 3-1. In some embodiments, when the protrusion 6-1 slides along the groove 3-1, the deformation trigger assembly 6 may contact and apply a force to the movable assembly 3, thereby causing the movable assembly 3 to deform.

In some embodiments, a length of the groove 3-1 may be positively correlated to a deformation degree range of the movable assembly 3. The length of the groove 3-1 refers to a length of the groove 3-1 along the direction y. Understandably, the longer the length of the groove 3-1 is, the longer the distance the protrusion 6-1 may slide along the groove 3-1, the greater the distance the booster assembly 4 may push and squeeze towards the movable assembly 3 along the direction y, and the greater the deformation degree range of the deformation that the movable assembly 3 undergoes may be. In some embodiments, the longer the protrusion 6-1 slides along the groove 3-1 is, the greater the thrust applied by the user to the booster mechanism (the press slider 9-1) may need to be.

In some embodiments of the present disclosure, the protrusion 6-1 may slide in the groove 3-1, and the length of the groove 3-1 may set, which may control the deformation degree of the movable assembly 3 more accurately, thereby ensuring that the booster mechanism has a suitable liquid injection speed.

In some embodiments, a liquid outlet of the liquid storage assembly may be in a shape of a convex circular arc.

The liquid outlet refers to an opening through which the injected liquid is discharged to an external environment. The external environment refers to an outside of the booster mechanism, and the shape of the convex circular arc refers to a shape of the liquid outlet in the external environment. In some embodiments, when the booster mechanism is in a striking state, a head end of the movable assembly 3 may have a convex deformation, i.e., a shape of the convex deformation of the head end of the movable assembly 3 may be the shape of the convex circular arc. The shape of the liquid outlet may be set as the shape of the convex circular arc, and a shape of the liquid outlet inside the booster mechanism may be set as a shape of a concave circular arc, which may increase a contact area between the movable assembly 3 and the liquid storage assembly 1, so that when the booster mechanism injects the liquid, the liquid storage assembly 1 may be fully squeezed by the movable assembly 3 to fully discharge the liquid to the external environment.

In some embodiments, an outer side of the movable assembly 3 may be made of a hydrophobic material. For example, the hydrophobic material may include silicone, polyurethane, polytetrafluoroethylene (PTFE), etc. In some embodiments, the outer side of the movable assembly 3 may be processed to make the processed outer side of the movable assembly 3 hydrophobic. For example, the outer side of the movable assembly 3 may be polished and sanded to make the processed outer side of the movable assembly 3 hydrophobic. As another example, a hydrophobic coating (e.g., a wax-based coating, or a nano-silica coating) may be covered on the outer side of the movable assembly 3. In some embodiments, the outer side of the movable assembly 3 may be made hydrophobic, which may ensure that the movable assembly 3 is not affected by water in the injected liquid and is capable of deforming normally to ensure that the liquid is injected normally.

The indicated orientations or positional relationships described herein are the orientations or positional relationships illustrated based on the accompanying drawings, which are merely intended to facilitate the description of the present disclosure and to simplify the description, and are not intended to indicate or imply that the devices or constructions referred to must have a particular orientation or be operated in a particular orientation configuration, and therefore cannot to be construed as a limitation of the present disclosure.

In the present disclosure, unless otherwise expressly specified and limited, the terms "connection," "provided," etc. should be understood in a broad sense, for example, may be a fixed connection, a detachable connection, or a one-piece; may be a mechanical connection, or an electrical connection; may be a direct connection or an indirect connection through an intermediate medium, and may be a communication within two components or an interactive relationship between two components. For those skilled in the art, the specific meaning of the above terms in the present disclosure may be understood according to specific conditions. One component may be directly on another component or indirectly on another component. When a component is referred to as "connected to" another component, the component may be directly connected to another component or indirectly connected to another component.

It should be understood that the indicated orientations or positional relationships of the terms "length," "width," "upper," "lower," "front," "rear," "left," "right," "vertical," "horizontal," "top," "bottom," "inside," "outside," etc. are the orientations or positional relationships illustrated based on the accompanying drawings, which are merely intended to facilitate the description of the embodiments of the present disclosure and to simplify the description, and are not intended to indicate or imply that the devices or components referred to must have a particular orientation, or be constructed and operated with a particular orientation, and therefore cannot to be construed as a limitation on the present disclosure.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A booster mechanism suitable for a liquid container, comprising a liquid storage assembly, wherein a tail end of the liquid storage assembly is provided with a strike space, the strike space is provided with a movable assembly, the movable assembly is capable of performing an axial movement along the strike space, and a tail end of the movable assembly is provided with:

- a booster assembly, wherein a front end of the booster assembly is provided with a deformation trigger assembly; and
- a deformation space, wherein
  - a deformation gap is between the deformation space and the deformation trigger assembly;
  - the deformation gap is configured to accommodate shrinkage deformation of the movable assembly;
  - the booster assembly includes a sealing reinforcement ring, the movable assembly is sleeved with the sealing reinforcement ring, an elastic modulus of the sealing reinforcement ring is greater than an elastic modulus of the movable assembly, so as to maintain airtightness of the strike space when the movable assembly deforms; and
  - the booster assembly comprises a thrust amplification member, the thrust amplification member comprises a press slider, a thrust slider, and a liquid channel, the liquid channel is filled with filling liquid, a contact area between the press slider and the filling liquid is smaller than a contact area between the thrust slider and the filling liquid, and the press slider is provided with an extension member extending into the liquid channel, a length of the extension member is used to adjust a height of the filling liquid in the liquid channel;
- a standby state, wherein when the booster mechanism is in the standby state, there is an interference fit between an outer side of the movable assembly and a side wall of the strike space; and
- a striking state, when the booster mechanism is in the striking state, a head end of the movable assembly has a convex deformation, and there is no interference fit between the outer side of the movable assembly and the side wall of the strike space.

2. The booster mechanism suitable for a liquid container of claim 1, wherein a connection between the deformation trigger assembly and the front end of the booster assembly is provided with a circular arc concave chamfer.

3. The booster mechanism suitable for a liquid container of claim 1, wherein the deformation space includes a cylindrical groove, and the deformation trigger assembly includes a cylindrical convex bar, and a diameter of the cylindrical convex bar is smaller than a diameter of the cylindrical groove.

4. The booster mechanism suitable for a liquid container of claim 1, wherein a plurality of airtight rings are distributed on the outer side of the movable assembly, and the plurality of airtight rings contact the side wall of the strike space when the booster mechanism is in the standby state.

5. The booster mechanism suitable for a liquid container of claim 4, wherein the plurality of airtight rings are distributed at an interval distance.

6. The booster mechanism suitable for a liquid container of claim 1, wherein the booster assembly is provided with a spring.

7. The booster mechanism suitable for a liquid container of claim 6, wherein an outer side of the booster assembly is provided with a press-slide member, one end of the spring is connected to the press-slide member, and another end of the spring is connected to the movable assembly.

8. The booster mechanism suitable for a liquid container of claim 1, wherein the liquid channel is provided with a connecting member, the connecting member is in a shape of a step, and the thrust slider is detachably connected to the connecting member, so as to adjust the contact area between the thrust slider and the filling liquid by replacing the thrust slider of different sizes.

9. The booster mechanism suitable for a liquid container of claim 1, wherein the booster mechanism includes a reminder device, the reminder device includes a shrapnel and card members; and the shrapnel and the card members contact to make a sound when the booster mechanism is in the striking state.

10. The booster mechanism suitable for a liquid container of claim 9, wherein the card members are disposed on an inner side of the liquid storage assembly, and the shrapnel is disposed on the outer side of the movable assembly or an outer side of the booster assembly.

11. The booster mechanism suitable for a liquid container of claim 10, wherein at least one of the card members is in a shape of a convex bar, the card members are disposed on an inner side of the movable assembly, and the shrapnel is disposed on the deformation trigger assembly, lengths of the card members decrease sequentially along an injection direction, and a number of times the shrapnel contacts the card members is positively correlated with a deformation degree of the movable assembly.

12. The booster mechanism suitable for a liquid container of claim 9, wherein

- the card members are distributed at an equal interval or a unequal interval along axial direction of the liquid storage assembly;

when the card members are distributed at the equal interval, a number of sounds corresponds to an injection dose;

when the card members are distributed at the unequal interval, a sound volume or a frequency corresponds to the injection dose or an injection speed; and a groove depth of the card members gradually decreases along an injection direction.

13. The booster mechanism suitable for a liquid container of claim 1, wherein the booster assembly includes a protrusion and the movable assembly includes a groove, the protrusion is slidably disposed in the groove, a length of the groove is positively related to a deformation degree range of the movable assembly, and the length of the groove limits a sliding stroke of the protrusion, thereby controlling a maximum shrinkage deformation amount of the movable assembly.

14. The booster mechanism suitable for a liquid container of claim 1, wherein a liquid outlet of the liquid storage assembly is in a shape of a convex circular arc.

15. The booster mechanism suitable for a liquid container of claim 1, wherein an outer side of the movable assembly is made of a hydrophobic material.

16. The booster mechanism suitable for a liquid container of claim 15, wherein the outer side of the movable assembly is covered with a hydrophobic coating, and the hydrophobic coating is a wax-based coating or a nano-silica coating.

17. The booster mechanism suitable for a liquid container of claim 1, wherein a thickness of the head end of the movable assembly is negatively correlated with a deformation degree of the convex deformation generated at the head end and negatively correlated with the deformation degree of shrinkage deformation generated around the head end, and the thickness of the head end is selected as needed according to viscosity of the filling liquid and an injection speed requirement.

* * * * *